(12) United States Patent
Boecker et al.

(10) Patent No.: US 6,729,188 B1
(45) Date of Patent: May 4, 2004

(54) CRIMP STRENGTH DESTRUCTIVE TEST MODULE

(75) Inventors: Karl Boecker, Bryan, OH (US); Gregg Thiel, Edgerton, OH (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 10/273,530

(22) Filed: Oct. 18, 2002

(51) Int. Cl.[7] .................................................. G01N 3/08
(52) U.S. Cl. ...................................................... 73/821
(58) Field of Search ........................... 73/821, 709, 800, 73/597, 602, 628, 806; 417/63; 359/1

(56) References Cited

U.S. PATENT DOCUMENTS 5,791,881 A * 8/1998 Moubayed et al. ............ 417/63

* cited by examiner

*Primary Examiner*—Edward Leekowitz
*Assistant Examiner*—Octavia Davis
(74) *Attorney, Agent, or Firm*—Mark W. Croll; Paul F. Donovan

(57) ABSTRACT

A testing module for destructively testing the crush strength of objects. Radially arranged fingers are moved against the object by rotation of a cam ring engaged against cam followers on the fingers. A hydraulic cylinder is connected to the cam ring, to rotate the cam ring. A load cell in one of the fingers records the force applied to the object until the object fails structurally.

21 Claims, 3 Drawing Sheets

CRIMP STRENGTH DESTRUCTIVE TEST MODULE

FIELD OF THE INVENTION

The present invention relates generally to testing apparatus, and more particularly, to an apparatus for destructive testing of the strength of parts subjected to crimping or crush forces in use.

BACKGROUND OF THE INVENTION

Molded plastic parts have attained wide spread use in many assemblies. With the ever-improving strength of plastic materials now available, plastic parts are used as structural components that must withstand significant force and or loads. The lighter weight and resistance to deterioration such as corrosion and rusting of plastic materials have made plastic parts preferable to metal parts in a variety of applications. For example, in the automotive industry, suspension systems can include hollow plastic parts to which a rubber or elastomeric boot is affixed by a clamping ring to effect a seal tight against internal hydraulic pressures. The force exerted on the plastic part during crimping of the clamping ring can be extremely high, particularly when steel rings are used. The plastic part must withstand such force.

When the plastic part is relatively thick, injection or fill speed can affect several physical qualities in the final product. Faster fill or injection speeds tend to provide a smoother surface finish, but can result in an increase in the presence of voids in the final product. Voids can lead to a reduction of strength in the part. Slower fill times tend to result in fewer voids, but a less smooth surface finish. Moreover, a generally smooth surface finish is often required to seal Brings for system pressure. Therefore, achieving a desired surface finish and strength in the final product can be a balance between competing needs.

In relatively thick parts it is virtually impossible to have a completely void free structure. However, the mere presence of voids does not necessarily mean the part is insufficiently strong for the intended application. Voids may be sufficiently small and sufficiently infrequent that the part will have adequate strength for its intended purpose. Further, the voids may be present in locations of relative insignificance. Therefore, while it is feasible to check all parts by x-ray or other techniques to determine the presence of voids, such testing is expensive, greatly increasing the manufacturing cost for the injection molded part, and the test is not a true indicator of the strength of the part.

When plastic parts are manufactured in batches from a single batch of materials, with each part formed under substantially similar conditions, all of the parts thus formed tend to exhibit substantially similar characteristics. This can be used advantageously for quality control testing in that a representative sample of parts from each batch can be subjected to testing, with the results thereof applied to all parts in the batch. If the tested parts pass quality control testing, all parts in the batch are deemed to have passed. On the other hand, if the representative sample fails testing, the entire batch from which the sample was selected is deemed to have failed, and will be scrapped. This approach to quality control testing, wherein only a sample and not all parts are tested, makes it possible to use destructive testing techniques on the samples. In destructive testing, the part is subjected to conditions of concern until the part fails. In this way, it can be determined not only if the established standards are met, but also if the standards are exceeded, and by how much. The manufacturing conditions can then be adjusted, if trends arc perceived from successive batches.

It is desirable to have a safe, efficient and rapid test method and apparatus for testing a representative sample of parts from manufacturing processes, which will determine the crush strength or crimp strength of the part at the location of significance on the part, to determine if the part meets standards or greatly exceeds standards. It is desirable that an apparatus therefore be adjustable for testing a variety of parts of different sizes.

SUMMARY OF THE INVENTION

The present invention provides a destructive testing module that operates efficiently and easily to perform crush strength testing at the critical area of a part, and that is adaptable for use with parts of different diameters.

In one aspect thereof, the invention provides a test module for destructive testing of a part. Fingers are arranged to define a center opening of a size to receive the part to be tested. Each finger has an inner end to engage the part, and an outer end. Each outer end has a cam follower engaged with a separate cam for each cam follower. The cams are adapted for operation in unison to drive the fingers in unison toward the center opening. A load cell is operatively connected to at least one finger, to measure load exerted on the part in the center opening. A reporting means is connected to the load cell for communicating the load sensed by the load cell.

In another aspect thereof, the invention provides a crush strength testing module with a ring having an inner face defining a plurality of cams, and a plurality of radially extending fingers. Each finger has a cam follower engaged against one of the cams. The inner ends of the fingers collectively define an opening therebetween. The cams and the fingers are adapted and arranged for simultaneous movement of the fingers radially inwardly in the ring, for decreasing the size of the opening upon rotation of the ring. A load cell is operatively connected to one of the fingers. A reporting means is connected to the load cell for reporting load sensed by the load cell. A drive means is connected to the ring, for rotating the ring and moving the fingers.

In still another aspect thereof, the invention provides a method for testing crush strength of a part, the method including said steps providing a plurality of fingers disposed radially about a central opening, each finger being movable radially toward the opening; providing cams and a drive means for moving the fingers in unison, and sensing means for ascertaining load force exerted on a part in the opening; positioning a part in said opening; moving the fingers against the part in unison, with sufficient force to cause structural failure of the part; and determining the load exerted against the part to cause the structural failure thereof.

An advantage of the present invention is providing a destructive testing apparatus that closely approximates the force applied to a part in regular use, and determines the actual crush resistance of the critical area of the tested part.

Another advantage of the present invention is providing a test module that is easy to use and adaptable for use with parts of different diameters.

Still another advantage of the present invention is providing an enclosed testing module that contains the broken pieces from a tested part, and thereby protects an operator of the module.

Other features and advantages of the invention will become apparent to those skilled in the art upon review of the following detailed description, claims and drawings, in which like numerals are used to designate like features.

Figure 1:
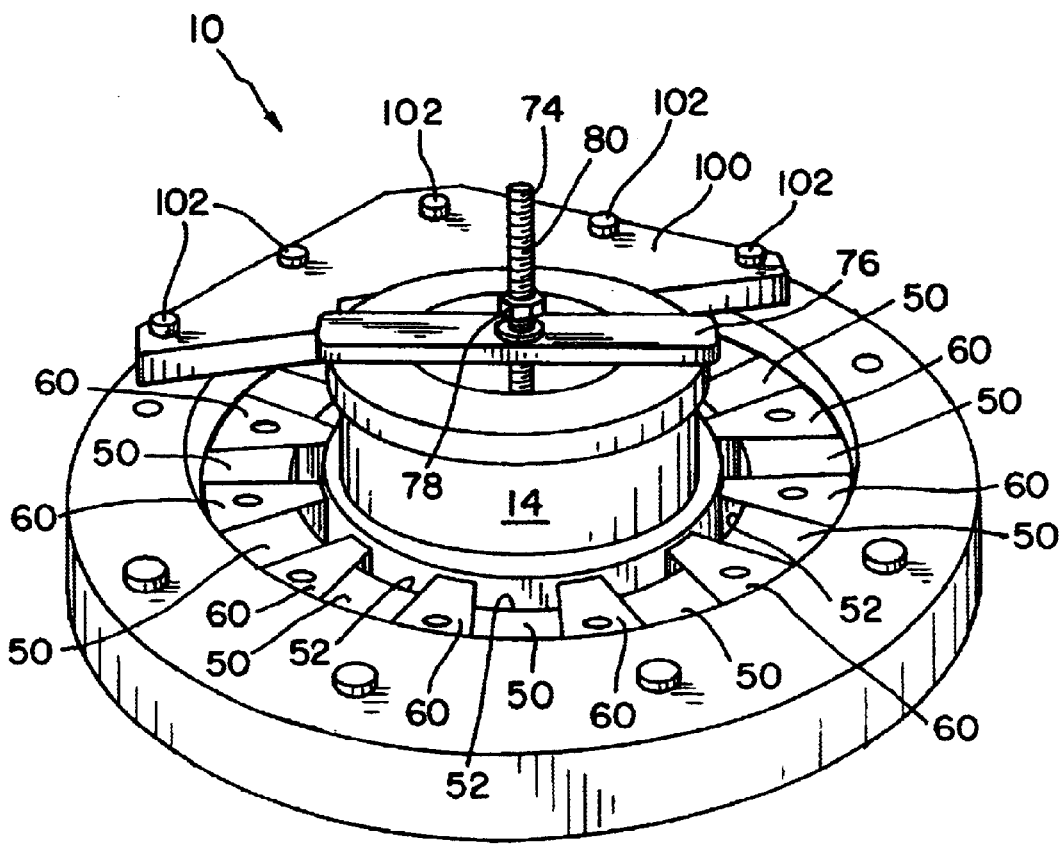
FIG. 1 is a perspective view of a test head in accordance with the present invention.

Before the embodiments of the invention are explained in detail, it is to be understood that the invention is not limited in its application to the details of construction and the arrangements of the components set forth in the following description or illustrated in the drawings. The invention is capable of other embodiments, and of being practiced or being carried out in various ways. Also, it is understood that the phraseology and terminology used herein are for the purpose of description and should not be regarded as limiting. The use herein of "including" and "comprising", and variations thereof is meant to encompass the items listed thereafter and equivalents thereof, as well as additional items and equivalents thereof.

DETAILED DESCRIPTION OF THE PREFERRED EMBODIMENT

Referring now more specifically to the drawings, and to FIG. 1 in particular, a test head 10 is shown for a testing module 12 (FIG. 2) in accordance with the present invention. Test head 10 is shown having a test part 14 positioned therein, for destructive testing in accordance with the present invention. While testing module 12 has particular utility, and can be used advantageously for testing hollow plastic parts 14, it can be used for testing the crush resistance of parts 14 made of other materials as well.

Testing module 12 includes, in addition to head 10, a drive mechanism 16 and sensor system 18, all confined within an enclosure 20. It should be understood that in a preferred embodiment for testing module 12, enclosure 20 completely surrounds at least test head 10. Depending on the material from which part 14 is made, the destructive testing of part 14 can be somewhat violent. When compressed to the point of failure, part 14 may shatter abruptly into numerous small fragments. At least head 10 should be confined within enclosure 20, to contain the fragments and shards that may burst from part 14 as it is tested to the point of failure. In this regard, enclosure 20 will have a bottom 22, walls 24 (illustrated by single lines in FIG. 2) and a top (not shown) of plastic to contain the fragments and shards created. Advantageously, enclosure 20 is made of clear plastic, so that the progress of a test, and the operation of testing module 12 can be observed readily.

Figure 2:
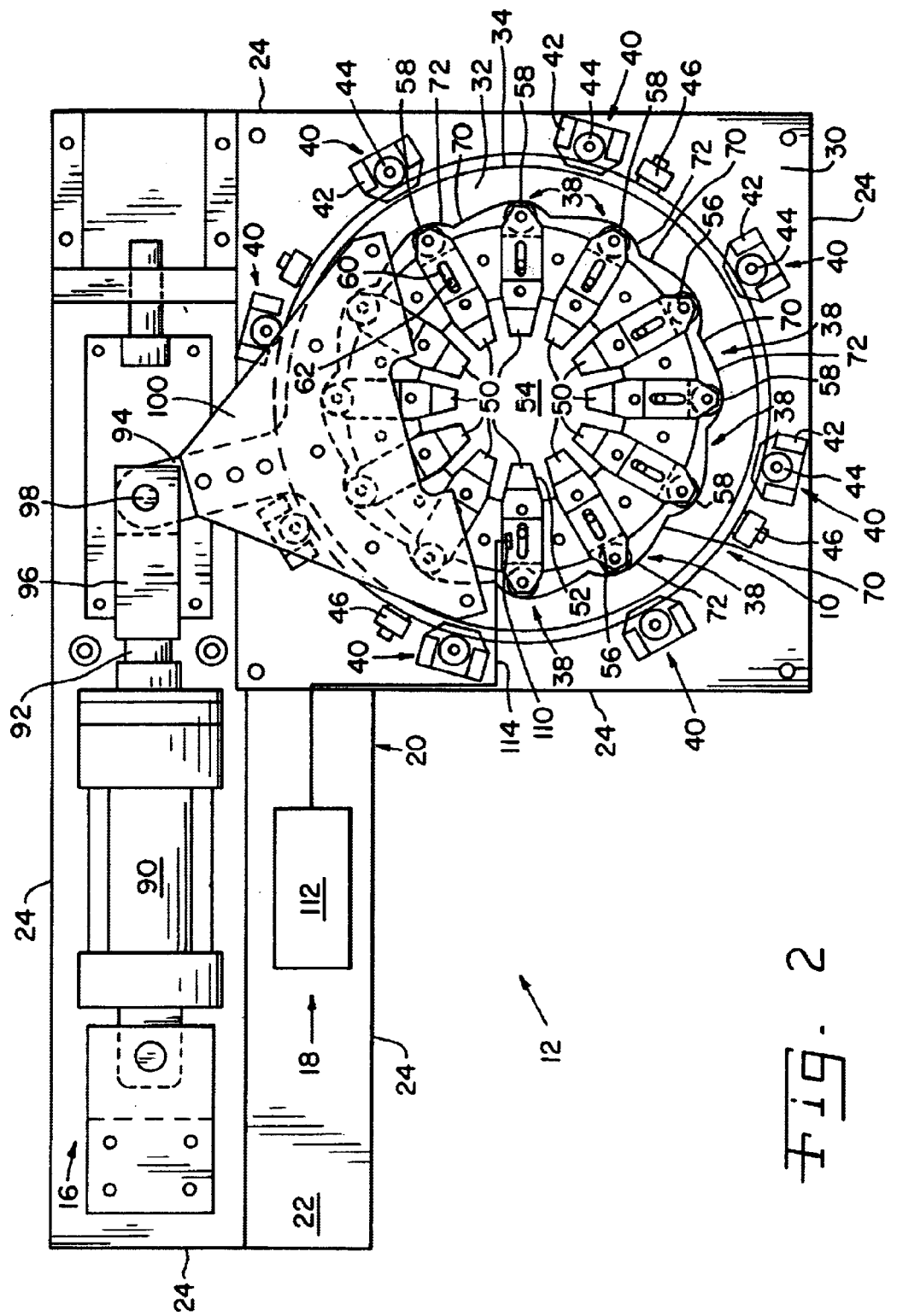
FIG. 2 is a plan view of testing module in accordance with the present invention.

Head 10 includes a base 30 and a movable cam ring 32 thereon. Cam ring 32 is mounted rotatably on base 30, and can be moved through a part rotation thereof. Cam ring 32 has an outer face 34 and an inner face 36 defining a plurality of cams 38, the details of which will be described in greater detail hereinafter. A plurality of trunnions 40 is disposed about outer face 34 of cam ring 32. Each trunnion 40 has a block 42 secured to base 30 and a wheel 44 rotatably disposed in block 42. Trunnion wheels 44 are disposed in engagement with outer face 34, to guide the rotation of cam ring 32. Between several pairs of adjacent trunnions 40, cam ring 32 is provided with stops 46 to limit the rotation of cam ring 32 to an arc limited to the distance that stops 46 can move between trunnions 40. Eight trunnions 40 are shown in FIG. 2, however it should be understood that more or fewer trunnions 40 can be used, and guide means other than trunnions 40 can be used for containing the movement of cam ring 32.

Head 10 further includes a plurality of radially arranged fingers 50 having inner ends 52 (FIG. 3) thereof defining a center opening 54 for receiving part 14 therein. Outer ends 56 of each finger 50 define cam followers 58 for riding against cams 38. Cam followers 58 can be in the form of wheels 58 or other structure allowing smooth translation along cams 38, as cam ring 32 is rotated. (For clarity of the drawing, in FIG. 2, not all parts of each finger 50 are identified with reference numerals.) While head 10 is illustrated with twelve fingers 50, more or fewer fingers 50 can be used. When part 14 is being tested for resistance to crushing from a ring or other clamping like force exerted on part 14, a sufficient number of fingers 50 should be used to closely simulate clamping by a ring.

Each finger 50 is adapted for radial movement both toward and away from center opening 54. Spacers 60 (FIG. 3) are provided to direct the linear movement of fingers 50. One spacer 60 is provided between fingers 50 of each pair of adjacent fingers 50. Further, a guide slot 62 (FIG. 2) is provided in each finger 50 for receiving a guide pin 64 from base 30. (Again, for purposes of clarity, not all slots 62 and pins 64 are identified with reference numbers in FIG. 2.)

Each inner end 52 is adapted to engage part 14, to apply compressive force thereto as fingers 50 are moved radially inwardly. Advantageously, center opening 54 has a depth for receiving part 14, and inner ends 52 are shaped so as to contact part 14 along the region at which force is applied to part 14 during normal use of part 14. In this way, the strength of each part 14 is tested at the region of part 14 that must withstand the compressive force during use.

Cams 38 effect the radial inward movement of fingers 50 as cam ring 32 is moved in a clockwise direction, as illustrated in FIG. 2. Each cam 38 is an arcuate surface having a shallow region 70 and a deep region 72 smoothly transitioning between each other. In FIG. 2, only some of the shallow regions 70 and deep regions 72 are identified with reference numerals, but it should be understood that each cam 38 is constructed similarly to the other cams 38. A cam 38 is provided for each finger 50, equally spaced about cam ring 32. Each cam 38 is equally dimensioned. Adjacent fingers 50 are equally spaced from each other, and are all of the same length. As a result, each cam follower 58 is similarly positioned on its associated cam 38, for any position of cam ring 32. As cam ring 32 is moved, all fingers 50 are moved similarly and in unison thereby. Stops 46 are positioned on cam ring 32 to restrain movement of cam ring 32 so that each cam follower is transitioned along a single cam 38, and can not jump from one cam 38 to an adjacent cam 38.

A post 74 extends from base 30 through the center of center opening 54, and a part 14 disposed in center opening 54. A hold down member 76, such as a bar 76, is secured to post 74, such as by a nut 78 engaging a threaded portion 80 on post 74. During use of testing module 12, hold down member 76 is positioned in close proximity to part 14, but is not tightened there against. Hold down member 76 restricts part 14 from rising, as compressive force is applied thereto. To install part 14 in center opening 54 for testing, nut 78 is unthreaded from post 74, and hold down member 76 is removed therefrom.

Drive mechanism 16 includes a hydraulic cylinder 90 having a shaft 92 connected to an arm 94 of cam ring 32 via a clevis 96 rigidly secured to shaft 92 and joined to arm 94 by a clevis pin 98. The connection between clevis 96 and arm 94 permits relative rotational movement about clevis pin 98. A gusset 100 is tied to arm 94 and cam ring 32 by fasteners 102, such as screws, bolts, rivets or the like. Alternatively, gusset 100 can be welded or otherwise attached in place. Gusset 100 is provided to reduce any tendency of cam ring 32 to distort as force is applied thereto by hydraulic cylinder 90, and resistance to the rotation thereof is experienced as inner ends 52 of fingers 50 encounter part 14.

Hydraulic cylinder 90 is a double acting cylinder, providing positive drive force for moving cam ring 32 in both clockwise and counterclockwise directions, as illustrated in FIG. 2. As shaft 92 is extended by hydraulic cylinder 90, cam ring 32, illustrated in FIG. 2, is rotated in the clockwise direction. Cams 38 are moved along cam followers 58, from deep regions 72 to shallow regions 70. Fingers 50 are caused to move radially inwardly, applying compressive force to part 14. When shaft 92 is retracted into cylinder 90, cam ring 32 is caused to rotate counterclockwise. Cams 38 are moved along cam followers 58, from shallow regions 70 to deep regions 72. Those skilled in the art will understand that fingers 50 can be spring loaded so as to automatically retract as cam ring 32 is rotated counterclockwise, and cam followers 58 transition from shallow regions 70 to deep regions 72.

Sensor system 18 includes a load cell 110 attached to one finger 50, to determine the force applied by the finger 50 to part 14. Load cell 110 is connected to a reporting means or communicating device 112 such as a display, printer, computer or the like via a conductor 114.

Figure 3:
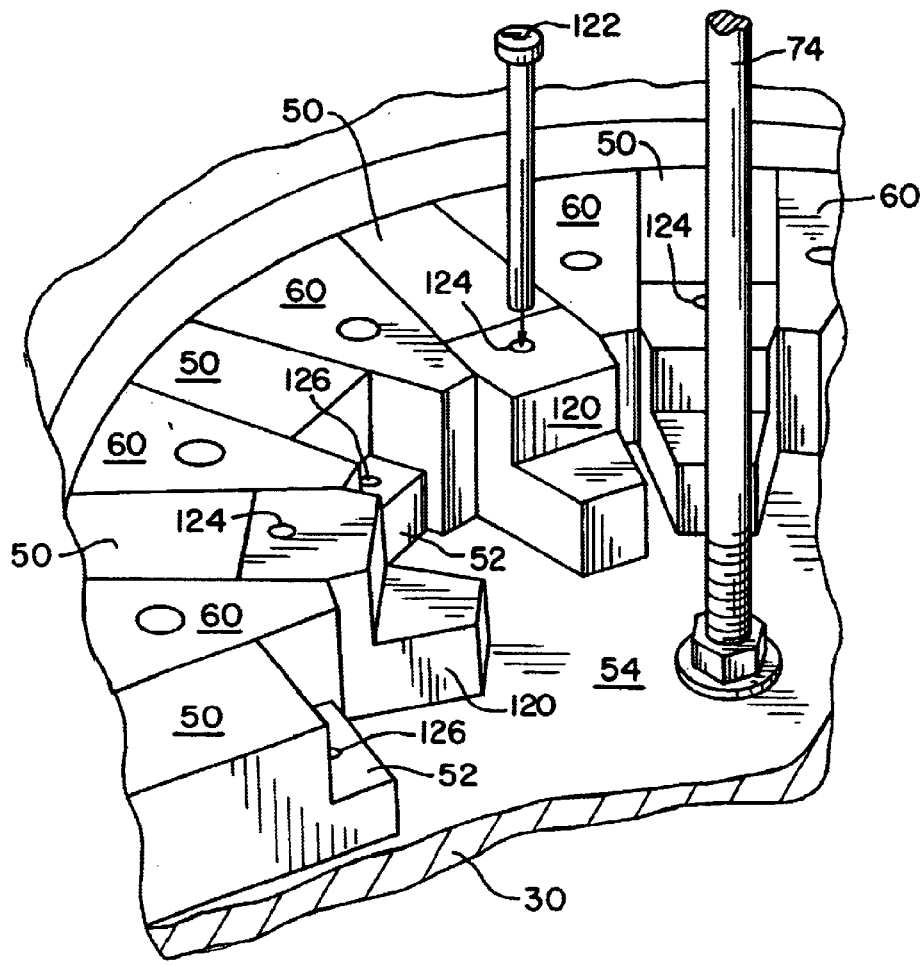
FIG. 3 is an enlarged fragmentary perspective view of a portion of the test head.

Test head 10 is adaptable for compressive testing of parts 14 of different diameters. Since the radial distance that each finger 50 can move is limited, it is necessary to lengthen each finger 50 for testing smaller diameter parts 14. FIG. 3 illustrates the manner in which each finger 50 can be lengthened or shortened to accommodate different diameter parts 14. Each finger 50 is provided with an extension 120 secured thereto by a pin 122. Pins 122 are inserted through holes 124 in extensions 120, and are anchored in holes 126 in fingers 50. Extensions 120 on each finger 50 increase the effective length of each finger 50 so that, for any position of cam followers 58 on cams 38, the diameter of center opening 54 is less than the diameter of center opening 54 when fingers 50 do not have extensions 120 thereon. Sets of extensions 120 can be provided of different lengths, to provide even greater versatility in the use of test module 12.

In the use of testing module 12 in accordance with the present invention, during the manufacturing process for making parts 14 in batches, a representative sample of each batch is selected for testing. Each selected part 14 is tested individually to its point of failure. Under rigid testing standards, if a single selected part from a batch fails testing, the entire batch from which the failed part 14 was selected is scrapped.

To install a selected part 14 for testing, nut 78 and hold down member 76 are removed from post 74. Part 14 is positioned in center opening 54 such that inner ends 52 align with the desired area of part 14 at which crush strength is to be measured. If necessary, the effective lengths of fingers 50 are increased by aligning an extension 120 with each finger 50, and securing each extension 120 to each finger 50 by inserting pin 122 in aligned holes 124 and 126. With part 14 properly positioned in center opening 54, hold down member 76 is inserted over post 74, and nut 78 is spun onto threaded portion 80 of post 74. Hold down member 76 is loosely fit above part 14.

From the shaft-retracted position illustrated in FIG. 2, hydraulic cylinder 90 is operated to extend shaft 92. Through the connection of clevis 96 to arm 94, linear movement of shaft 92 is translated to rotational movement of cam ring 32. The application of force from hydraulic cylinder 90 is increased until the compressive force exerted by fingers 50 causes part 14 to fail structurally. The force measured by sensor system 18 is compared against standards established for the part 14. If selected part 14 was caused to break below the standard established therefor, the tested part 14 is judged to have failed the test. If the selected and tested part 14 breaks at a force greater than that established for parts 14, the selected and tested part is determined to have passed the test.

The present invention provides a testing module and test procedure for testing representative samples of parts to determine the actual strength performance of the tested parts. From the tested performance, judgements arc made about the batches of parts from which the samples were selected.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention, and will enable others skilled in the art to utilize the invention. The claims are to be construed to include alternative embodiments to the extent permitted by the prior art.

Various features of the invention are set forth in the following claims. It is understood that the phraseology and terminology used herein are for the purpose of description and should not be regarded as limiting. The use of "including" and "comprising" and variations thereof herein is meant to encompass the items listed thereafter and equivalents thereof as well as additional items and equivalents thereof.

Various features of the invention arc set forth in the following claims.

What is claimed is:

1. A test module for destructive testing of a part, comprising:

a plurality of fingers radially arranged to define a center opening, said center opening being of a size to receive the part to be tested, each said finger having an inner end to engage the part and an outer end, each said outer end having a cam follower;

a cam for each said cam follower, said cams adapted for operation in unison to drive said fingers in unison toward said center opening;

a load cell operatively connected to at least one said finger to measure load exerted on the part in said center opening; and reporting means connected to said load cell for communicating the load sensed by said load cell.

2. The test module of claim 1, including a ring surrounding said fingers, with said cams provided on said ring, and said test module including drive means for rotating said ring.

3. The test module of claim 2, said drive means including a hydraulic cylinder connected to said ring.

4. The test module of claim 2, said ring having an outer face and inner face, with said cams defined by said inner face; and said module including a plurality of rollers rotatably engaged against said outer face of said ring.

5. The test module of claim 4, said drive means including a hydraulic cylinder connected to said ring.

6. The test module of claim 5, including a post in said central opening, and a hold down member secured to said post above a part to be tested.

7. The test module of claim 5, said fingers being separated by spacers.

8. The test module of claim 5, said fingers having inner ends, and said module including extensions attached to said inner ends of said fingers.

9. The test module of claim 1, said fingers having inner ends, and said module including extensions attached to said inner ends of said fingers.

10. The test module of claim 9, including a ring surrounding said fingers, with said cams provided on said ring, and said test module including drive means for rotating said ring.

11. A crush strength testing module comprising:

a ring having an inner face defining a plurality of cams;

a plurality of radially extending fingers, one said finger for each said cam, each said finger having a cam follower engaged against one of said cams, said inner ends collectively defining an opening therebetween;

said cams and said fingers adapted and arranged for simultaneous movement of said fingers radially inwardly in said ring, for decreasing the size of said opening upon rotation of said ring;

a load cell operatively connected to one of said fingers;

reporting means connected to said load cell for reporting load sensed by said load cell; and drive means connected to said ring for rotating said ring and moving said fingers.

12. The crush strength testing module of claim 11, including removable extensions on said fingers.

13. The crush strength testing module of claim 11, said drive means including a hydraulic cylinder.

14. The crush strength testing module of claim 13, including replaceable extensions said fingers.

15. The crush strength testing module of claim 11, including an enclosure surrounding said ring and said fingers, for containing pieces of a part tested in said module.

16. The crush strength testing module of claim 11, including a post disposed in said opening and a hold down member secured to said post.

17. A method for testing crush strength of parts, said method comprising said steps of:

providing a plurality of fingers disposed radially about a central opening, each said finger being movable radially toward said opening;

providing cams and a drive means for moving said fingers in unison, and sensing means for ascertaining load force exerted on a part in said opening;

positioning one of the parts in said opening;

moving said fingers against the part in unison, with sufficient force to cause structural failure of the part; and determining the load exerted against the part to cause the structural failure thereof.

18. The test method of claim 17, including providing cam followers on radially outward ends of the fingers and a ring have the cams thereon, and moving the fingers by rotating the ring.

19. The test method of claim 18, including providing an extension for each finger and attaching the extensions to the fingers dependent upon a size of the part to be tested.

20. The test method of claim 17, including providing an extension for each finger and attaching the extensions to the fingers dependent upon a size of the part to be tested.

21. The test method of claim 17, including selecting a representative sample of parts from a batch of parts, and obtaining the part for testing from the representative sample of parts.

* * * * *